(12) United States Patent
Kitazawa et al.

(10) Patent No.: US 9,140,670 B2
(45) Date of Patent: Sep. 22, 2015

(54) ULTRASONIC INSPECTION METHOD AND ULTRASONIC INSPECTION DEVICE

(75) Inventors: So Kitazawa, Mito (JP); Naoyuki Kono, Mito (JP); Atsushi Baba, Tokai (JP)

(73) Assignee: HITACHI-GE NUCLEAR ENERGY, LTD., Ibaraki (JP)

( * ) Notice: Subject to any disclaimer, the term of this patent is extended or adjusted under 35 U.S.C. 154(b) by 930 days.

(21) Appl. No.: 12/975,414

(22) Filed: Dec. 22, 2010

(65) Prior Publication Data

US 2011/0166807 A1 Jul. 7, 2011

(30) Foreign Application Priority Data

Jan. 5, 2010 (JP) ................................. 2010-000475

(51) Int. Cl.
*G06F 19/00* (2011.01)
*G01N 29/06* (2006.01)
*G01N 29/26* (2006.01)
*G01N 29/44* (2006.01)

(52) U.S. Cl.
CPC .......... *G01N 29/0663* (2013.01); *G01N 29/262* (2013.01); *G01N 29/4409* (2013.01); *G01N 2291/105* (2013.01)

(58) Field of Classification Search
CPC .......... G01N 29/0663; G01N 29/4409; G01N 29/262
USPC .............................................. 702/56; 73/606
See application file for complete search history.

(56) References Cited

U.S. PATENT DOCUMENTS

| 2006/0123912 | A1* | 6/2006 | Karasawa et al. | ............... | 73/602 |
| 2006/0219013 | A1* | 10/2006 | Baba et al. | ..................... | 73/618 |
| 2009/0003665 | A1* | 1/2009 | Berg et al. | ..................... | 382/128 |
| 2009/0293621 | A1* | 12/2009 | Kitazawa et al. | ............... | 73/606 |

FOREIGN PATENT DOCUMENTS

| JP | 2005-98768 A | 4/2005 |
| JP | 2006-132973 A | 5/2006 |

OTHER PUBLICATIONS

M. Kondo et al., Digital signal processing with measurement sensor, Digital Signal Processing Series, vol. 12, pp. 143-186, Jan. 1993.

(Continued)

*Primary Examiner* — Patrick Assouad
*Assistant Examiner* — Haidong Zhang
(74) *Attorney, Agent, or Firm* — Mattingly & Malur, PC (57) ABSTRACT

An ultrasonic inspection method and an ultrasonic inspection device allow three-dimensional inspection data and three-dimensional shape data to be appropriately positioned on a display screen and allow a defect echo and a shape echo to be quickly identified even when information on the relative positions of a probe and an object to be inspected is not provided. The ultrasonic inspection data that is generated from the waveforms of ultrasonic waves received by an ultrasonic probe is compared with a plurality of ultrasonic propagation data pieces calculated by a ray tracing method on the basis of the three-dimensional shape data on an object to be inspected. The position of the three-dimensional inspection data or the three-dimensional shape data is moved relative to the other data position on the basis of the comparison results, thereby displaying the three-dimensional inspection data and the three-dimensional shape data while overlapping each other.

11 Claims, 8 Drawing Sheets

(56) References Cited

OTHER PUBLICATIONS

A. Baba et al., Development of 3-Dimensional Ultrasonic Testing System "3-D Focus-UT", Japan Society of Maintenology, The Fifth Scientific Lecture Meeting, Summary Report, 155 (2008).

A. Potts et al., Presentation and analysis enhancements of the NDT Workbench a software package for ultrasonic NDT data, Review of Progress in Quantitative Nondestructive Evaluation: vol. 19, AIP Conference Proceedings, vol. 509, pp. 741-748 (2000).

Kitazawa et al.; "Three-Dimensional Phased Array Ultrasonic Inspection System"; Inspection Technology; Feb. 1, 2009; vol. 14, No. 2; pp. 23-27, with partial English-language translation.

Touma et al.; "Inspection Technology for Nuclear Power Plant"; System/Control/Information; Mar. 15, 2009; vol. 53; No. 3; pp. 96-102, with partial English-language translation.

* cited by examiner

ULTRASONIC INSPECTION METHOD AND ULTRASONIC INSPECTION DEVICE

BACKGROUND OF THE INVENTION

1. Field of the Invention

The present invention relates to an ultrasonic inspection method and an ultrasonic inspection device. The invention more particularly relates to an ultrasonic inspection method in which an array type ultrasonic probe is used, and an ultrasonic inspection device that includes an array type ultrasonic probe.

2. Description of the Related Art

In recent years, constructional materials and the like are inspected by an ultrasonic inspection method. Such a method having being developed more accurately generates an image inside of an object to be inspected in a short time to inspect the inside of the object, as typified by a phased array method and an aperture synthesis method (refer to, for example, Non-Patent Document 1 (Digital signal processing series, volume 12, "Digital signal processing with measurement sensor" pp 143-186, issued by Shokodo, written by Michimasa Kondo, Yukimasa Ohashi, and Akio Jitsumori)).

The phased array method is based on a principle in which an array type ultrasonic probe having a plurality of piezoelectric elements is used and wavefronts of ultrasonic waves transmitted from the piezoelectric elements interfere with each other to form a synthesized wavefront that propagates. Thus, in the phased array method, timings of transmission of ultrasonic waves from the piezoelectric elements are controlled to delay so that timing of each transmission is shifted, thereby enabling control on incident angles of the ultrasonic waves and also focusing of the ultrasonic waves.

For reception of ultrasonic waves, incident angles of ultrasonic waves that are reflected, and received by the piezoelectric elements are shifted in timing and is summed, thereby enabling control on the incident angles to be formed when the ultrasonic waves are received and also reception of the ultrasonic waves in focused state, as is the case with the transmission.

A linear scanning method and a sector scanning method are generally known as the phased array method. The linear scanning method is such that piezoelectric elements for a one-dimensional array probe linearly scan an object to be inspected. The sector scanning method is such that a direction in which an ultrasonic wave is transmitted or received is changed within a fan-shaped region. If a two-dimensional array probe that has piezoelectric elements arranged in a matrix pattern is used, ultrasonic waves can be three-dimensionally focused on any position and thereby scanning suitable for an object to be inspected can be performed. Each of the two methods allows ultrasonic waves to be scanned at high speed without moving the ultrasonic probe. Also, each of the two methods allows incident angles of ultrasonic waves and the vertical position at a focal point thereof to be controlled without replacing the ultrasonic probe. These methods are techniques which enable inspection to be performed at high speed with high accuracy.

The aperture synthesis method is based on the following principle: when a piezoelectric element transmits an ultrasonic wave in such a manner that the ultrasonic wave spreads in an object to be inspected and the piezoelectric element receives the reflected ultrasonic wave, a defect that is the source from which the received reflected ultrasonic wave derives is present on a circular arc that has a center thereof at the position of the piezoelectric element (that transmitted and received the ultrasonic wave) and has a radius of a distance that the reflected ultrasonic wave propagates. The piezoelectric element transmits an ultrasonic wave and receives the reflected ultrasonic wave while the position of the piezoelectric element is sequentially changed. The ultrasonic waves received by the piezoelectric element at the positions are calculated by an electronic computer so that the ultrasonic waves are represented by circular arcs. Intersections on the circular arcs are concentrated at the position of a defect that is the source from which the reflected ultrasonic waves derive, whereby the position of the defect is specified. The details of the calculation performed by the electronic computer are described in Non-Patent Document 1.

In the methods in which a probe that has a plurality of piezoelectric elements is used, the probe can three-dimensionally receive an ultrasonic wave signal reflected from a defect without a movement of the probe. However, in order to specify the three-dimensional position of the defect on the basis of the reflected ultrasonic wave signal, the three-dimensional position of the defect is estimated on the basis of a two-dimensional image having multiple reflection intensity distributions of waves reflected at locations that are spatially different from each other. Alternatively, the three-dimensional position of the defect is estimated by converting the reflection intensity distributions into three-dimensional data and then three-dimensionally displaying the three-dimensional data.

When the linear scanning method and the sector scanning method based on phased array methods are adopted, multiple two-dimensional reflection intensity images responsive to known scanning pitches can be acquired. Thus, a direction in which a reflected ultrasonic wave appears can be specified by sequentially selectively displaying the two-dimensional reflection intensity images on a screen. However, these methods have limitations when three-dimensional scanning other than the aforementioned scanning is performed.

To cope with this, advancement in computer technology in recent years has made available a technique for performing interpolation on ultrasonic wave signals reflected and received from multiple directions so that image data that indicates points three-dimensionally arranged in a matrix pattern is generated and displaying the image data by volume rendering or surface rendering. In addition, there is a technique for displaying an image as a three-dimensional point group without conversion of the reflected ultrasonic wave signals into data that indicates points arranged in a matrix pattern. Since the techniques are designed such that the data is stored as three-dimensional inspection data, an inspector can confirm the three-dimensional inspection data in any direction after the measurement (refer to, for example, Non-Patent Document 2 ("Development of 3-Dimensional Ultrasonic Testing System "3D Focus-UT"", Japan Society of Maintenology, The fifth scientific lecture meeting, Summary report, 155 (2008), written by Atsushi Baba, So Kitazawa, Naoyuki Kono, Yuji Adachi, Mitsuru Odakura, and Osamu Kikuchi) and Non-Patent Document 3 (Potts, A; McNab, A.; Reilly D.; Toft, M., "Presentation and analysis enhancements of the NDT Workbench a software package for ultrasonic NDT data", REVIEW OF PROGRESS IN QUANTITATIVE NONDESTRUCTIVE EVALUATION: Volume 19. AIP Conference Proceedings, Volume 509, pp. 741-748 (2000)).

However, it is difficult to determine, only on the basis of such three-dimensional inspection data, whether or not a wave that corresponds to a peak of a reflection intensity distribution is a wave reflected on an end surface or boundary surface of an object to be inspected or is a wave reflected on a defect. Especially, it is difficult even for an experienced inspector to make such a determination for inspection of an object having a complex shape, since reflected ultrasonic wave signals (shape echoes) dependent on the shape of the object appear in great numbers. Thus, software has been developed that allows data (three-dimensional shape data) on the three-dimensional shape of an object (to be inspected) to be displayed together with three-dimensional inspection data. By overlapping and comparing the two types of the data using this software, it is possible to easily determine whether an ultrasonic wave signal is a shape echo or an echo (defect echo) generated from a defect. Data generated by a general-purposed computer aided design (CAD) system is read and used for three-dimensional shape data in many cases (refer to, for example, Non-Patent Documents 2 and 3).

SUMMARY OF THE INVENTION

However, the three-dimensional inspection data and the three-dimensional shape data are generated using different coordinate systems. In order to overlap and display the three-dimensional inspection data and the three-dimensional shape data, it is necessary to perform positioning correction by moving the three-dimensional inspection data or the three-dimensional shape data to an appropriate position on a display screen. If the correction is not appropriately performed, it is not possible to confirm the correlation between the three-dimensional inspection data and the three-dimensional shape data. Thus, it is not possible to identify a shape echo and a defect echo. In a conventional technique, an inspector performs a positioning correction operation using a display device so as to change coordinate values of the three-dimensional inspection data and coordinate values of the three-dimensional shape data on the basis of numerical information on the relative positions of a probe and an object (to be inspected). This operation is repeatedly performed until identification of a shape echo and a defect echo can be attained; it disadvantageously takes much time to identify the echoes.

Especially in a case where the numerical information on the relative positions of the probe and the object to be inspected is not provided, a problem arises that is how to adjust the positions of the probe and the object to be inspected. The case is, for example, that a welded part located inside a pressure container included in a boiling water reactor (BWR) is inspected from an outer surface of the pressure container. A cylindrical structure which is called a core shroud is provided in a central region of the pressure container of the BWR in order to hold a steam-water separator and a steam dryer which are located on the upper side of the pressure container so as to surround reactor core. The core shroud is held on the lower side of the pressure container by a ring-shaped structure called a shroud support. Further, the shroud support is welded and fixed to the pressure container. In recent years, a problem arose that is about countermeasures to be taken against light water reactors that are in a operating condition for a long passage of time in Japan. As the countermeasures, the importance of nondestructive inspection of structures in reactors with ultrasonic waves has been increased. For example, it is necessary to inspect whether or not a crack or the like is generated in a welded part between a shroud support and a pressure container. In general, the pressure container is filled with light water, and structures are provided at a high density in a reactor. Thus, it is difficult to inspect the welded part from the inside of the pressure container. Therefore, a technique for inspecting, with ultrasonic waves, a welded part from an outer surface of a pressure container has been proposed. In the technique, as mentioned above, the efficiency of inspection is significantly improved by displaying three-dimensional inspection data acquired by a probe placed on the outer surface of the pressure container, together with CAD data on the pressure container and the shroud support, since this allows discrimination easy between a shape echo and a defect echo. The position adjustment of the three-dimensional inspection data and the CAD data is required to be performed with millimeter accuracy on a display screen. However, it is not possible to detect, with millimeter accuracy, the position of the probe relative to the position of the welded part located inside the large pressure container.

An object of the present invention is to provide an ultrasonic inspection method and an ultrasonic inspection device, which allow position adjustment of three-dimensional inspection data and three-dimensional shape data to be appropriately performed on a display screen, thereby allowing identification of a defect echo and a shape echo quickly performed even when information on the relative positions of a probe and an object to be inspected is not provided.

(1) In order to accomplish the aforementioned object, according to the present invention, an ultrasonic inspection method includes the steps of:

preparing an ultrasonic probe;

generating three-dimensional ultrasonic inspection data from waveforms of ultrasonic waves received by the ultrasonic probe;

calculating a plurality of ultrasonic propagation data pieces on the basis of three-dimensional shape data on an object to be inspected;

comparing the generated three-dimensional ultrasonic inspection data with the calculated plurality of ultrasonic propagation data pieces; and displaying the three-dimensional ultrasonic inspection data and the three-dimensional shape data in such a manner as to move on a display screen a position at which to display the three-dimensional ultrasonic inspection data or the three-dimensional shape data.

In the ultrasonic inspection method, it is possible to perform position adjustment of the three-dimensional inspection data and the three-dimensional shape data even when information on the relative positions of the probe and the object to be inspected is not provided, thereby making it possible to quickly identify a shape echo and a defect echo.

(2) The ultrasonic inspection method described in the item (1) preferably further includes the steps of: calculating differences between the three-dimensional ultrasonic inspection data and the ultrasonic propagation data pieces; specifying an ultrasonic propagation data piece from which the smallest difference among the calculated differences has been calculated; and displaying the three-dimensional ultrasonic inspection data and the three-dimensional shape data in such a manner as to move on the display screen a position at which to display the three-dimensional ultrasonic inspection data or the three-dimensional shape data based a result of the specifying.

(3) The ultrasonic inspection method described in the item (2) preferably further includes the steps of: calculating a mutual correlation function from the three-dimensional ultrasonic inspection data and the ultrasonic propagation data pieces; calculating a power spectral density function from the mutual correlation function; calculating the differences between the three-dimensional ultrasonic inspection data and the ultrasonic propagation data pieces on the basis of the power spectral density function; and specifying an ultrasonic propagation data piece from which the smallest difference among the calculated differences has been calculated.

(4) The ultrasonic inspection method described in the item (3) preferably further includes the steps of: moving in parallel and rotating the three-dimensional ultrasonic inspection data or the three-dimensional shape data relative to the other data so that an ultrasonic wave incident point and ultrasonic wave incident direction of the specified ultrasonic propagation data piece match an ultrasonic wave incident point and ultrasonic wave incident direction of the three-dimensional shape data; and displaying the three-dimensional ultrasonic inspection data and the three-dimensional shape data while the three-dimensional ultrasonic inspection data and the three-dimensional shape data overlap each other.

(5) In order to accomplish the aforementioned object, an ultrasonic inspection method includes the steps of:

preparing an ultrasonic probe;

generating two-dimensional ultrasonic inspection data from waveforms of ultrasonic waves received by the ultrasonic probe;

calculating a plurality of ultrasonic propagation data pieces on the basis of three-dimensional shape data on an object to be inspected;

comparing the generated two-dimensional ultrasonic inspection data with the calculated plurality of ultrasonic propagation data pieces;

moving a position at which to display the two-dimensional ultrasonic inspection data or the three-dimensional shape data relative to the other data position on a display screen; and three-dimensionally displaying the two-dimensional ultrasonic inspection data and the three-dimensional shape data while the two-dimensional ultrasonic inspection data and the three-dimensional shape data overlap each other.

(6) In order to accomplish the aforementioned object, an ultrasonic inspection method includes the steps of:

preparing an ultrasonic probe;

generating two-dimensional ultrasonic inspection data from waveforms of ultrasonic waves received by the ultrasonic probe;

calculating a plurality of ultrasonic propagation data pieces on the basis of three-dimensional shape data on an object to be inspected;

comparing the generated two-dimensional ultrasonic inspection data with the calculated plurality of ultrasonic propagation data pieces;

moving a position at which to display the two-dimensional ultrasonic inspection data or the three-dimensional shape data relative to the other data position on a display screen; and displaying the two-dimensional inspection data and an outline of a cross sectional image of the three-dimensional shape data in an overlapping manner.

(7) In the ultrasonic inspection method described in any of the items (1) to (3), it is preferable that the ultrasonic propagation data pieces be calculated by a ray tracing method on the basis of the three-dimensional shape data on the object to be inspected.

(8) In order to accomplish the aforementioned object, an ultrasonic inspection device includes: an ultrasonic probe that includes a plurality of piezoelectric elements; a pulser that supplies transmission signals to the respective piezoelectric elements of the ultrasonic prove; a receiver that receives signals from the respective piezoelectric elements of the ultrasonic prove; a delay time controller that sets delay times which are deferent from each other for each of the piezoelectric elements, to the transmission signals and to the signals received by the piezoelectric elements; a data storage unit that stores the waveforms of ultrasonic waves received by the ultrasonic probe; a calculator that is provided for image processing and generates inspection data from the waveforms stored in the data storage unit; a display unit that simultaneously displays three-dimensional shape data on an object to be inspected and the inspection data; and an analyzing calculator that calculates ultrasonic propagation data pieces on the basis of the three-dimensional shape data, wherein the display unit has a position correcting function of automatically moving positions of the three-dimensional shape data and the inspection data relative to each other on a display screen.

In the ultrasonic inspection device, it is possible to perform position adjustment of the three-dimensional inspection data and the three-dimensional shape data even when information on the relative positions of the probe and the object to be inspected is not provided, thereby making it possible to quickly identify a shape echo and a defect echo.

(9) The ultrasonic inspection device described in the item (8) preferably further includes a moving unit that is fixed to the ultrasonic probe and moves the ultrasonic probe in any direction, wherein the inspection data and the three-dimensional shape data are displayed while overlapping each other.

(10) The ultrasonic inspection device described in the item (8) preferably further includes a moving unit that is fixed to the ultrasonic probe and moves the ultrasonic probe in any direction, wherein the inspection data and an outline of a cross sectional image of the three-dimensional shape data are displayed while overlapping each other.

(11) In the ultrasonic inspection device described in the item (8), it is preferable that the ultrasonic propagation data pieces be calculated by a ray tracing method on the basis of the three-dimensional shape data.

The present invention allows position adjustment of three-dimensional inspection data and three-dimensional shape data even when information on the relative positions of a probe and an object to be inspected is not provided, thereby making it possible to quickly identify a shape echo and a defect echo.

DESCRIPTION OF THE PREFERRED EMBODIMENTS

The configuration and operations of an ultrasonic inspection device according to a first embodiment of the present invention are described below with reference to FIGS. 1 to 9.

First, the entire configuration of the ultrasonic inspection device according to the first embodiment is described with reference to FIGS. 1 to 6.

Figure 1:
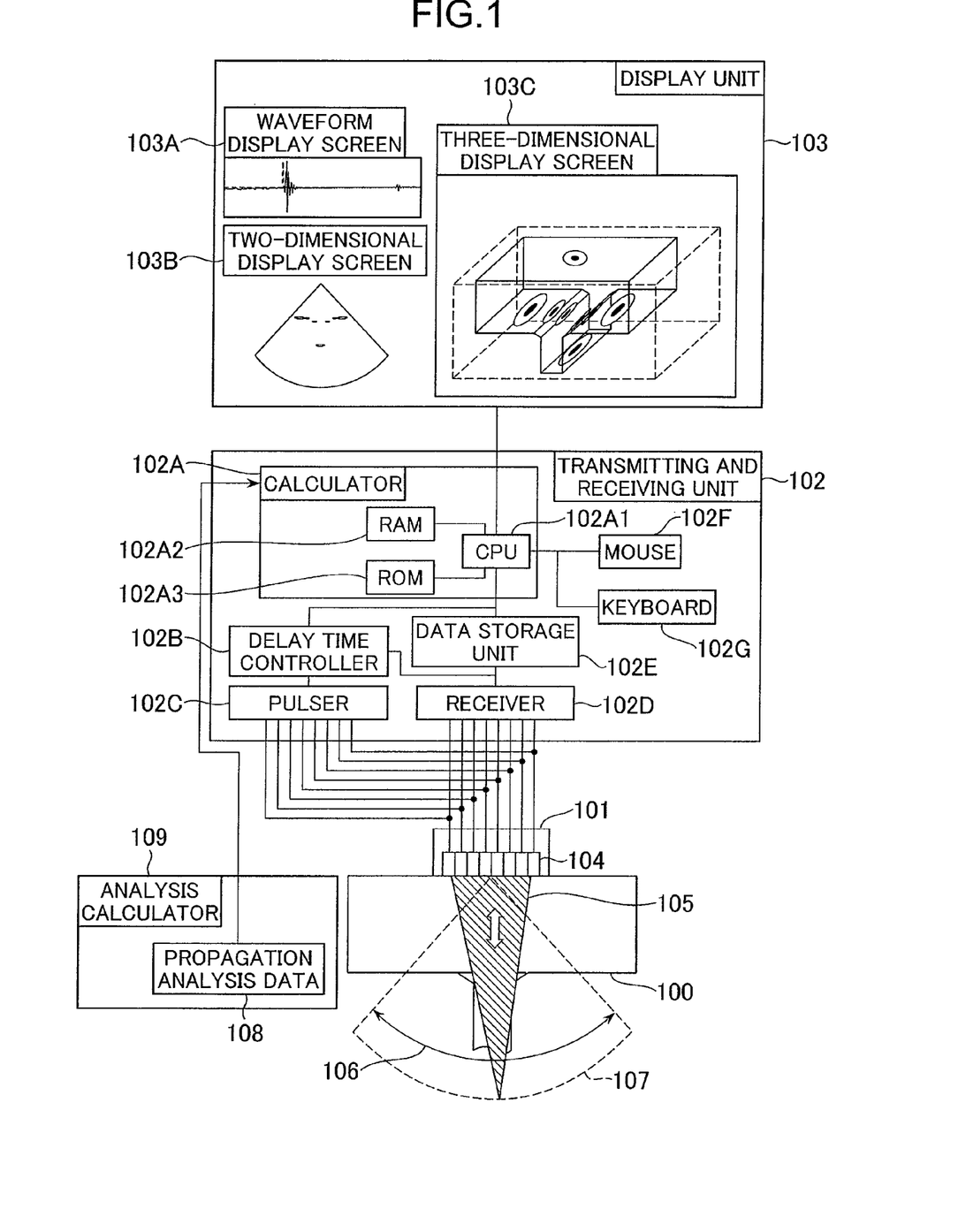
FIG. 1 is a diagram showing the entire configuration of an ultrasonic inspection device according to a first embodiment of the present invention.
Figure 2:
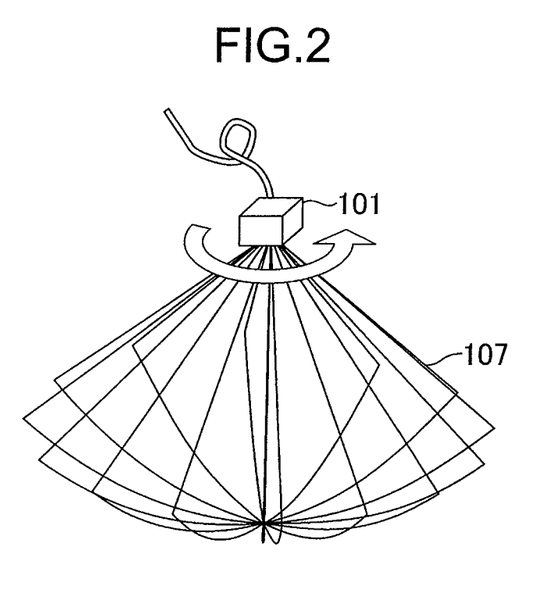
FIG. 2 is a diagram showing a scanning method in which the ultrasonic inspection device according to the first embodiment acquires three-dimensional inspection data.
Figure 3:
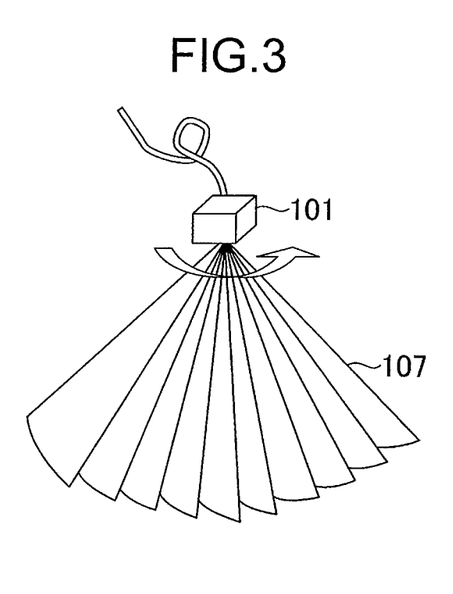
FIG. 3 is a diagram another scanning method in which the ultrasonic inspection device according to the first embodiment acquires the three-dimensional inspection data.
Figure 4:
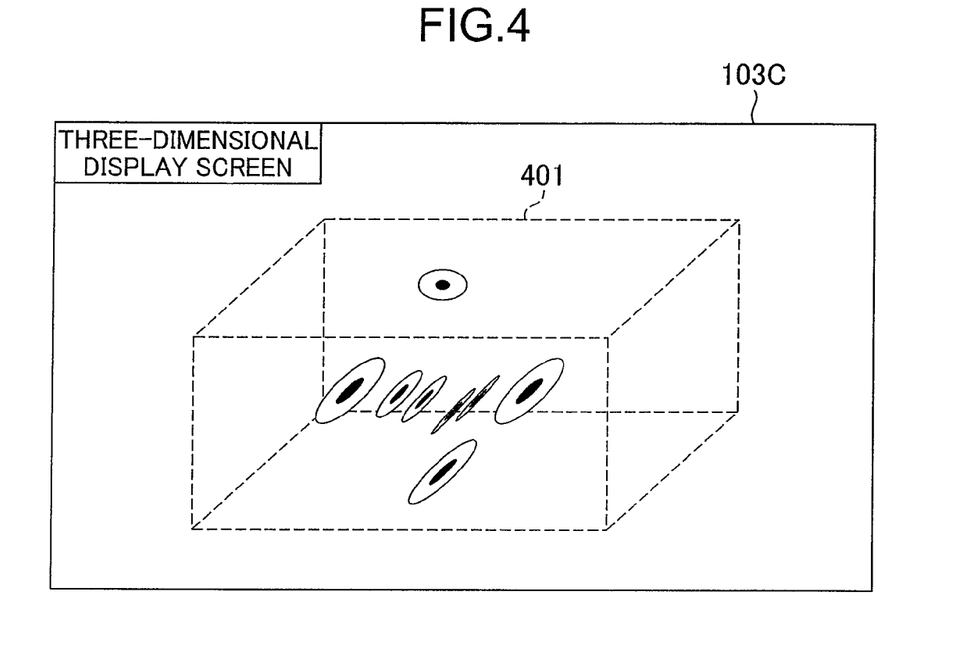
FIG. 4 is a diagram showing an example of display of the three-dimensional inspection data in the ultrasonic inspection device according to the first embodiment.
Figure 5:
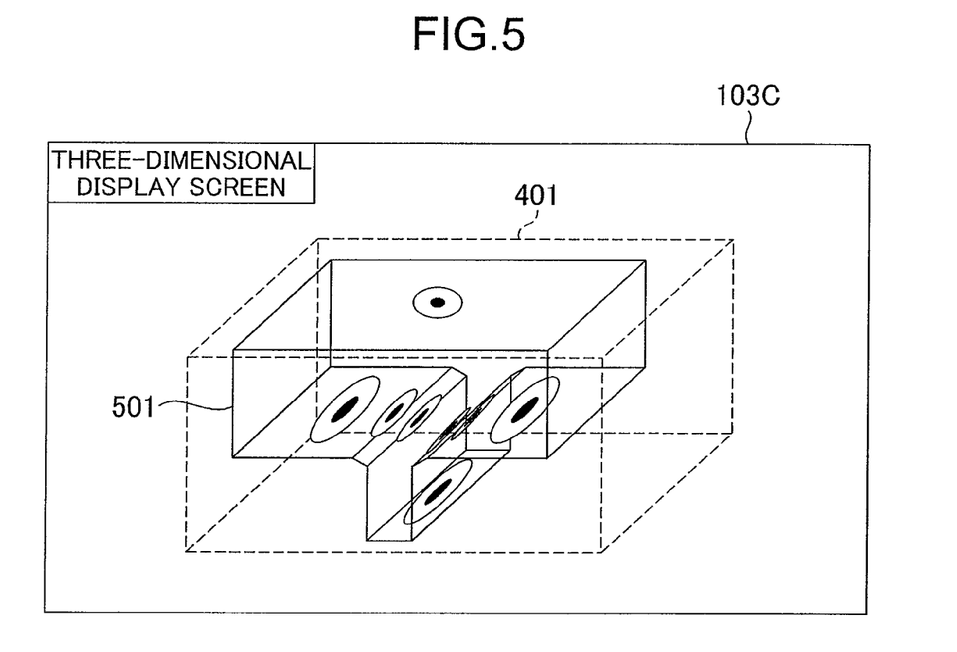
FIG. 5 is a diagram showing an example of display of the three-dimensional inspection data and three-dimensional shape data in the ultrasonic inspection device according to the first embodiment.
Figure 6:
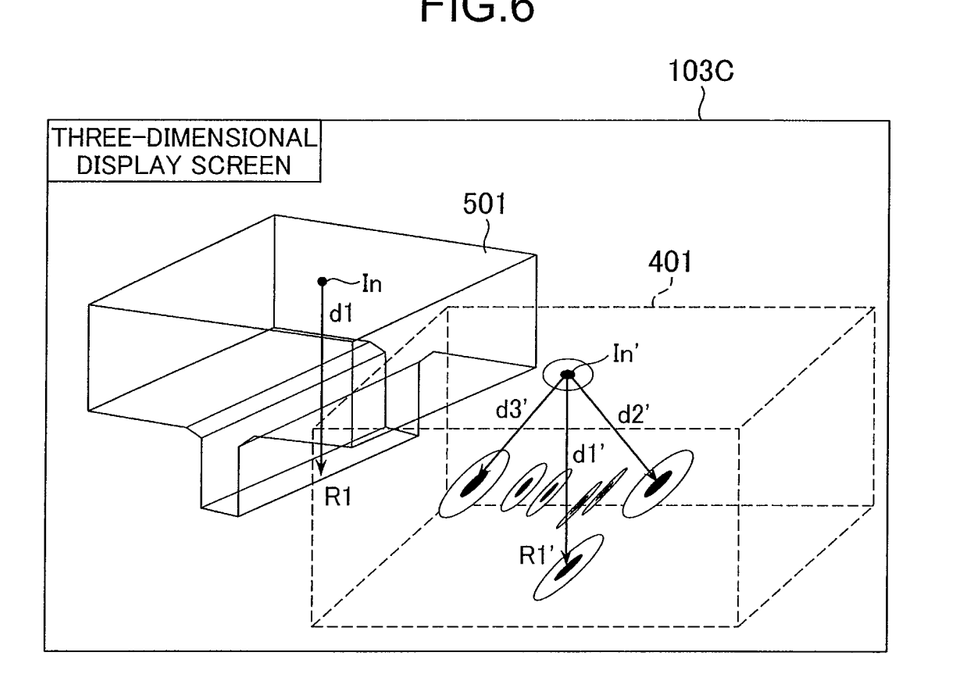
FIG. 6 is a diagram showing an example of display of the three-dimensional inspection data and the three-dimensional shape data in the ultrasonic inspection device according to the first embodiment.

FIG. 1 is a diagram showing the entire configuration of the ultrasonic inspection device according to the first embodiment. FIGS. 2 and 3 are diagrams each showing a scanning method in which the ultrasonic inspection device according to the first embodiment acquires three-dimensional inspection data. FIG. 4 is a diagram showing an example of display of the three-dimensional inspection data in the ultrasonic inspection device according to the first embodiment. FIGS. 5 and 6 are diagrams each showing an example of display of the three-dimensional inspection data and three-dimensional shape data in the ultrasonic inspection device according to the first embodiment.

The ultrasonic inspection device according to the present embodiment includes an array type ultrasonic probe 101, a transmitting and receiving unit 102 and a display unit 103. The array type ultrasonic probe 101 transmits ultrasonic waves so that the ultrasonic waves are incident on an object 100 to be inspected. The display unit 103 displays received signal and an image (inspection image) on the object 100 to be inspected.

As shown in FIG. 1, the array type ultrasonic probe 101 includes a plurality of piezoelectric elements 104 that each generate and receive an ultrasonic wave. The array type ultrasonic probe 101 is placed on a surface (hereinafter also referred to as an inspection surface) of the object 100 to be inspected. After that, the array type ultrasonic probe 101 receives driving signals from the transmitting and receiving unit 102 and generates ultrasonic waves 105 on the basis of the driving signals. Then, the array type ultrasonic probe 101 causes the generated ultrasonic waves to propagate in the object 100 to be inspected. The array type ultrasonic probe 101 detects, as received signals, the waves reflected from the object 101. The array type ultrasonic probe 101 transmits the received signals to the transmitting and receiving unit 102. In FIG. 1, the array type ultrasonic probe 101 is in direct contact with the object 100 to be inspected. However, the array type ultrasonic probe 101 may be in contact with the object 100 through a wedge made of a material through which an ultrasonic wave can pass.

The transmitting and receiving unit 102 causes the array type ultrasonic probe 101 to transmit and receive ultrasonic waves. The transmitting and receiving unit 102 includes a calculator 102A, a delay time controller 102B, a pulser 102C, a receiver 102D and a data storage unit 102E. The pulser 102C supplies driving signals to the array type ultrasonic probe 101. The receiver 102D processes signals transmitted from the array type ultrasonic probe 101.

The calculator 102A basically includes a CPU 102A1, a RAM 102A2 and a ROM 102A3. A program that controls the CPU 102A1 is written in the ROM 102A3. The CPU 102A1 reads necessary external data from the data storage unit 102E according to the program written in the ROM 102A3. In addition, the CPU 102A1 receives data from the RAM 102A2, executes arithmetic processing on the received data, and outputs the processed data to the data storage unit 102E.

The CPU 102A1 controls the delay time controller 102B, the pulser 102C and the receiver 102D so that the delay time controller 102B, the pulser 102C and the receiver 102D perform necessary operations. The delay time controller 102B controls the timings of outputting driving signals from the pulser 102C and the timings of inputting received signals to the receiver 102D. Thus, the array type ultrasonic probe 101 can perform an operation according to a phased array method.

The operation that is performed by the array type ultrasonic probe 101 according to the phased array method is an operation of controlling incident angles 106 of ultrasonic waves 105 and the depth of a point at which the ultrasonic waves 105 are focused, transmitting the ultrasonic waves 105, and receiving the reflected ultrasonic waves 105. Thus, the receiver 102D receives signals from the array type ultrasonic probe 101 and supplies the received signals to the data storage unit 102E.

As described above, in phased array methods, various types of scanning can be performed by changing delay times. A linear scanning method in which the ultrasonic waves 105 propagate in parallel in order to acquire two-dimensional inspection data is known as one of the phased array methods. In addition, a sector scanning method in which the ultrasonic waves 105 propagate within a sector 107 is known as another one of the phased array methods.

For example, as shown in FIG. 2, scanning is performed to acquire three-dimensional inspection data so that the sector 107 is treated as a basic unit and rotated around a central axis of the probe 101. In addition, as shown in FIG. 3, scanning is performed to acquire three-dimensional inspection data so that the sector 107 is moved in a fan-shaped region. Various types of scanning other than the linear scanning and the sector scanning can be performed on the basis of the shape of the object 100 to be inspected.

Signals that are received by performing those types of scanning are transmitted to the data storage unit 102E, stored in the data storage unit 102E as stored data, and transmitted to the calculator 102A. The calculator 102A performs, on the basis of delay times, synthesis processing on the waveforms of the signals received by the piezoelectric elements, performs appropriate interpolation on the waveforms of the signals for the incident angles of the respective ultrasonic waves, and generates two-dimensional inspection data (pixel format inspection data including a two-dimensional square lattice as a unit) or three-dimensional inspection data (voxel format inspection data including a three-dimensional square lattice as a unit). Then, the calculator 102A converts the generated data into an image and causes the display unit 103 to display the image.

The display unit 103 includes a two-dimensional display screen 103B, a three-dimensional display screen 103C and a waveform display screen 103A. The two-dimensional inspection data is displayed on the two-dimensional display screen 103B. The three-dimensional inspection data is displayed on the three-dimensional display screen 103C. The waveform signals of the ultrasonic waves received by the piezoelectric elements are displayed on the waveform display screen 103A. In FIG. 1, the ultrasonic inspection device includes one display unit 103. However, the waveform display screen 103A, the two-dimensional display screen 103B and the three-dimensional display screen 103C may be included in display units, respectively. In this case, the display units are separately provided in the ultrasonic inspection device according to the present embodiment.

As shown in FIG. 4, three-dimensional inspection data 401 is displayed on the three-dimensional display screen 103C included in the display unit 103. A mouse 102F and a keyboard 102G are connected to the calculator 102A. Data can be entered into the calculator 102A by means of the mouse 102F or the keyboard 102G so that the size of an image of the three-dimensional inspection data 401 on the display screen is increased or reduced to any size. In addition, data can be entered into the calculator 102A by means of the mouse 102F or the keyboard 102G so that the color and transparency of the image of the three-dimensional inspection data 401 are optionally changed. The color of the image on the display screen can be changed according to a reflection intensity of wave. In this case, an inspector can select a color pattern from among multiple color patterns on the basis of the purpose of use.

Three-dimensional writing algorithms that are used to display the three-dimensional inspection data are achieved in libraries such as OpenGL (registered trademark) and DirectX (registered trademark). OpenGL and DirectX are industry-standard graphics application programming interfaces (graphics APIs) for graphics applications. When the graphics APIs are used in a program, and necessary information such as the shape of an object to be displayed, a viewpoint and the position of the object to be displayed is provided, the position, color, transparency and size of the image of the three-dimensional inspection data can be selected, and the three-dimensional inspection data can be displayed on the three-dimensional display screen 103C.

As shown in FIG. 5, the display unit 103 can simultaneously display the three-dimensional inspection data 401 and three-dimensional shape data 501 on the three-dimensional display screen 103C. The three-dimensional shape data 501 indicates the shape of the object 100 to be inspected. The inspector can use the mouse 102F or the keyboard 102G and enter data so that the color and transparency of an image of the three-dimensional shape data 501 are changed. In addition, the inspector can enter a value by using the keyboard 102G or drag the three-dimensional shape data 501 by using the mouse 102F so that the three-dimensional shape data 501 can be moved in parallel or rotated on the three-dimensional display screen 103C. In addition, the inspector can switch between displaying of the three-dimensional shaped data 501 and hiding of the three-dimensional shaped data 501 when necessary. Thus, the inspector can easily view the three-dimensional inspection data 401 even when the three-dimensional inspection data 401 and the three-dimensional shape data 501 overlap each other.

When CAD data on the object 100 to be inspected is present as the three-dimensional shape data, the CAD data can be read from the outside of the calculator 102A to be displayed. The format of the CAD data is a data format that allows the CAD data to be input and output by commercially available CAD software. For example, the format of the CAD data is stereolithography (STL) format or stand triangulated language (STL) format. STL formats allow the CAD data to be input and output by many types of CAD software. The format of the CAD data is STL format and represents surfaces of an object by using a group of many triangles. Surface normal vectors of the triangles and coordinate values of the three corners of each of the triangles are written in a STL file. The three-dimensional shape data 501 can be easily read from the STL file and displayed using the graphics APIs by writing multiple triangles.

As shown in FIG. 6, in general, coordinate systems of the three-dimensional inspection data 401 and the three-dimensional shape data 501 are different from each other. Thus, each pieces of data are displayed at different positions on the three-dimensional display screen 103C in a initial condition. The inspector can control by trial and error by using the keyboard 102G to enter values or using the mouse 102F so that the three-dimensional inspection data 401 and the three-dimensional shape data 501 are located at desired positions on the three-dimensional display screen 103C. Though this operation takes a long time and a lot of trouble, an automatic position adjustment process according to the present invention makes this operation easier. In addition, even when information on the relative positions of the probe and the object to be inspected is not provided in such a case, as described, as inspection from the outer surface of the pressure container included in the BWR is required, automatic position adjustment of the three-dimensional inspection data 401 and the three-dimensional shape data 501 is possible.

The process of automatic position adjustment of the three-dimensional inspection data 401 (shown in FIG. 6) and the three-dimensional shape data 501 (shown in FIG. 6) is described below in detail.

In general, in order to appropriately perform position adjustment of images of two data pieces, a standard coordinate system is set, and parallel movement and rotational movement are performed in combination with each other. Although a coordinate system of any one of the two data pieces is set as the standard coordinate system in many cases, any coordinate system may be set. Note that, the scale sizes of the images of the two data pieces match each other in this case. In case of parallel movement, determination of a vector that indicates amount of the movement and direction of the movement is necessary. On the other hand, in case of rotational movement, determination of a rotational axis and a rotational angle is necessary. The automatic position adjustment process according to the present invention is as follows. Ultrasonic propagation analysis (hereinafter referred to as propagation analysis) is performed all over a region to be inspected on the coordinate system of the three-dimensional data 501 in the same scanning manner as a measurement by sequentially changing an ultrasonic wave incident point and an ultrasonic wave incident direction. Then, after multiple propagation analysis data pieces acquired by the propagation analysis and measured waveform data pieces are sequentially compared with each other for each propagation paths, the best matching combination of measured waveform data pieces and propagation analysis data pieces, in which the two kinds of data pieces averagely match each other, is detected in the entire three-dimensional inspection data 401 or in a specified region. Based on the ultrasonic wave incident point and the ultrasonic incident direction that have been used for the propagation analysis of the aforementioned combination, the three-dimensional inspection data 401 or the three-dimensional shape data 501 is moved relative to the other data. The propagation analysis widely known is also called ray tracing analysis in which reflection and refraction of ultrasonic waves are calculated on the basis of a geometric theory by means of information on the shape and material of the object to be inspected as parameters to calculate propagation paths and propagation times of the ultrasonic waves.

In addition, the propagation analysis data pieces can be obtained by a finite element method or a boundary element method, in addition to the ray tracing analysis. For example, a sound field change in the object 100 to be inspected with respect to time is calculated by the finite element method and changes in the amplitudes of the ultrasonic waves at the positions of the piezoelectric elements 104 with respect to time are shifted at the same timings as that in measurement and summed. In this manner, the waveform data pieces can be obtained, which are similar to or the same as those obtained by the phased array method.

Next, the automatic position adjustment method in which the ultrasonic inspection device according to the present embodiment is used is described with reference to FIGS. 7 to 9.

Figure 7:
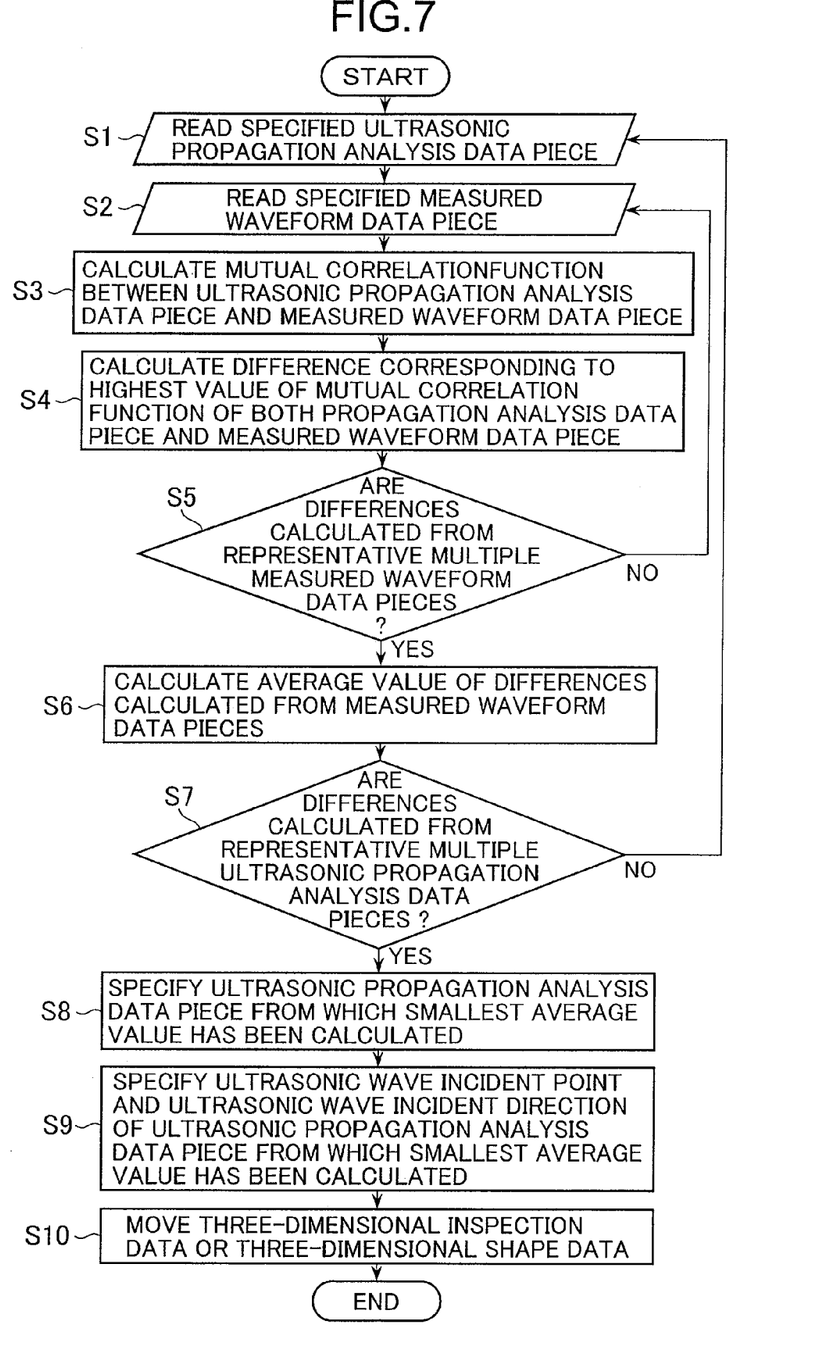
FIG. 7 is a flowchart of an automatic position adjustment method that is performed by the ultrasonic inspection device according to the first embodiment.

FIG. 7 is a flowchart of the automatic position adjustment method that is performed by the ultrasonic inspection device according to the first embodiment. FIG. 8 is a diagram showing measured waveform data pieces and propagation analysis data pieces, which are used in the automatic position adjustment method performed by the ultrasonic inspection device according to the first embodiment. FIG. 9 is a diagram showing a power spectral density function that is used in the automatic position adjustment method performed by the ultrasonic inspection device according to the first embodiment.

First, a first propagation analysis data piece 108 that is calculated by an analysis calculator 109 is read into a program executed by the calculator 102A (in step S1). The analysis may be performed by the calculator 102A for measurement control. The first propagation analysis data piece 108 includes: a position of a point at which an ultrasonic wave that propagates in a corresponding propagation path is reflected and refracted; a direction in which the reflection and the refraction occur; a distance from a point on which the ultrasonic wave is incident; a time from the incidence; and the like.

Next, a first measured waveform data piece is read into the program (in step S2).

Figure 8:
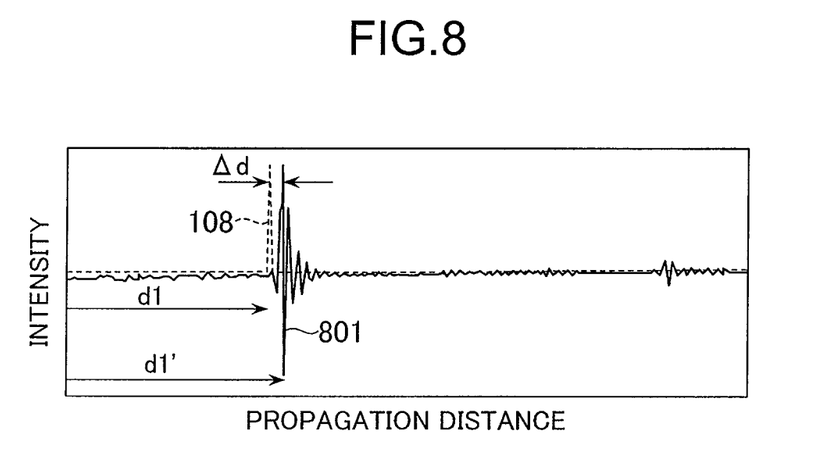
FIG. 8 is a diagram showing measured waveform data pieces and propagation analysis data pieces, which are used in the automatic position adjustment method performed by the ultrasonic inspection device according to the first embodiment.

FIG. 8 shows an example of the first measured waveform data piece 801 and an example of the first propagation analysis data piece 108. A propagation distance to a peak position of the first measured waveform data piece 801 is indicated by d1' and a propagation distance to a peak position of the first propagation analysis data piece 108 is indicated by d1. As the peak positions of the first measured waveform data piece 801 and the first propagation analysis data piece 108 shown in FIG. 8 do not match each other, there arises difference Δd between the two peak positions. When incident points of the ultrasonic waves and directions in which the ultrasonic waves propagate match each other between a measured data and an analyzed data, the peak positions of the data pieces 108 and 801 match or are very close to each other.

The propagation distance d1' to the peak position of the first measured waveform data piece 801 corresponds to a distance d1' between an ultrasonic wave incident point In' and a certain defect in the three-dimensional inspection data 401 shown in FIG. 6. The propagation distance d1 to the peak position of the first propagation analysis data piece 108 corresponds to a distance d1 between an ultrasonic wave incident point In and a position at which a defect has occurred in the three-dimensional shape data 501 shown in FIG. 6. Note that the propagation distance is calculated on the basis of a sound velocity and the distance between the ultrasonic wave incident point and the defect. When a temperature is changed, the sound velocity is also changed. Therefore, when a temperature during the measurement and a temperature set before the start of the measurement are slightly different from each other, the propagation distance d1' to the peak position of the first measured waveform data piece 801 is different from the propagation distance d1 to the peak position of the first propagation analysis data piece 108. In addition, when a difference of a set position of the array type ultrasonic probe 101 also generates a difference mentioned above. Note that the difference is very small.

The difference Δd between the propagation distances can be calculated on the basis of a mutual correlation function R expressed by the following equation (1) (in step S3). When the first propagation analysis data piece 108 is indicated by "f" and the first measured waveform data piece 801 is indicated by "g", the mutual correlation function R is calculated from the following equation (1) using Fourier transform F of the first propagation analysis data piece 108 and Fourier transform G of the first measured waveform data piece 801.

$$R=FT^{-1}\{F^*G\} \quad (1)$$

In the equation (1), "$FT^{-1}\{\ \}$" indicates inverse Fourier transform and F* indicates a complex conjugate of F. Normally, the first propagation analysis data piece 108 and the first measured waveform data piece 801 are discrete numerical data. Thus, discrete Fourier transform is performed in order to calculate the mutual correlation function R by the calculator 102A. As the mutual correlation function R is calculated as a complex number, it includes a real part and an imaginary part. In order to calculate the difference Δd between the propagation distances to the peak positions, however, a power spectral density function $|R|^2$ of the mutual correlation function R is used.

Figure 9:
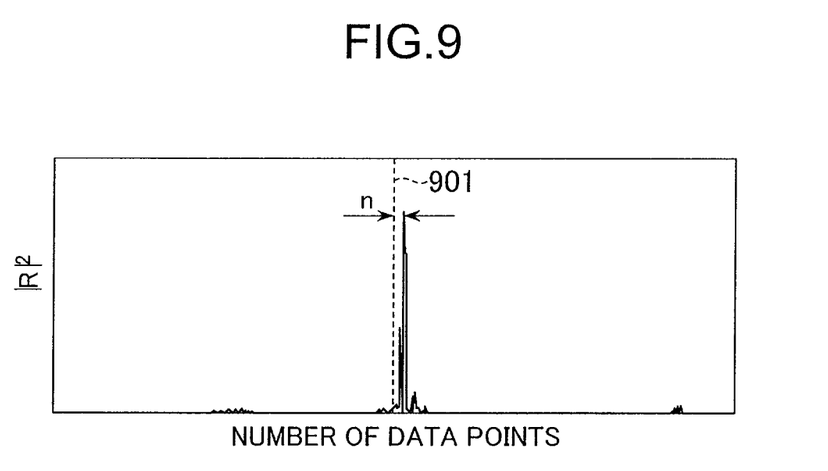
FIG. 9 is a diagram showing a power spectral density function that is used in the automatic position adjustment method performed by the ultrasonic inspection device according to the first embodiment.

FIG. 9 shows the power spectral density function $|R|^2$ calculated for the first propagation analysis data piece 108 and the first measured waveform data piece 801. The abscissa of the graph shown in FIG. 9 indicates the number of data points. The data points each have a data point number. The central value of the data point numbers is indicated by 901. The number n of data points between the central value 901 and a peak value of the power spectral density function $|R|^2$ corresponds to the difference Δd (in step S4). That is to say, when the first propagation analysis data piece 108 or the first measured waveform data piece 801 is shifted relative to the other data piece by the number n, the best matching of the peak positions can be obtained. In this example, the number of noticeable echo signals included in the first measured waveform data piece 801 is one, however, when the number thereof is two or more, the mutual correlation function R indicates multiple peaks. Likewise, in the case of the first propagation analysis data piece 108, the mutual correlation function R indicates multiple peaks. When either the first propagation analysis data piece 108 or the first measured waveform data piece 801 does not include a peak, the power spectral density function $|R|^2$ is not calculated. When the power spectral density function $|R|^2$ indicates multiple peaks, it is not ensure that the difference Δd between the propagation distances to the peak positions is accurately calculated. In order to avoid this problem, steps S2 to S4 are repeatedly performed on representative multiple measured waveform data pieces so as to calculate differences Δd between the propagation distances to the peak positions (in step S5). Then, the average value day of the differences Δd is calculated (in step S6). Preferably, calculation should be performed on all measured waveform data pieces to obtain differences Δd.

In this manner, the average value day of the first propagation analysis data piece is calculated.

Then, steps S2 to S6 are performed on second and third propagation analysis data pieces so as to calculate average values day according to the second and third propagation analysis data pieces (in step S7). Then, a propagation analysis data piece from which the smallest average value day has been calculated is specified (in step S8). Then, an ultrasonic wave incident point and an ultrasonic wave incident direction, which are set for calculation of the propagation analysis data piece from which the smallest average value day has been calculated, are specified (in step S9).

Lastly, the three-dimensional inspection data or the three-dimensional shape data is moved on the basis of the ultrasonic wave incident point and the ultrasonic wave incident direction which are calculated in step S9 to perform position adjustment, thereby displaying both of the data pieces on the three-dimensional display screen as shown in FIG. 5 (in step S10).

For example, when the propagation analysis data piece from which the smallest average value day is calculated is a part of three-dimensional shape data 501 shown in FIG. 6 and indicates that the ultrasonic wave is incident on the ultrasonic wave incident point In and propagates in an ultrasonic wave incident direction R1 a propagation distance d1, the three-dimensional inspection data 401 is moved in parallel so that the ultrasonic wave incident point In of the three-dimensional shape data 501 (shown in FIG. 6) matches an ultrasonic incident point In' of the three-dimensional inspection data 401 (shown in FIG. 6). Then, the three-dimensional inspection data 401 is rotationally moved so that the ultrasonic wave incident direction R1 connecting the ultrasonic wave incident point In to a position at which the defect has occurred in the three-dimensional shape data 501 shown in FIG. 6 matches an ultrasonic wave incident direction R1' connecting the ultrasonic wave incident point In' to the position of the certain defect in the three-dimensional inspection data 401 shown in FIG. 6, for example. In this manner, the automatic position adjustment of the three-dimensional inspection data and the three-dimensional shape data is performed.

As described above, according to the present embodiment, the three-dimensional inspection data generated from the waveforms of the ultrasonic waves received by the ultrasonic probe is compared with the multiple ultrasonic propagation analysis data pieces calculated by the ray tracing method on the basis of the three-dimensional shape data on the object to be inspected, and the three-dimensional inspection data or the three-dimensional shape data is automatically moved on the three-dimensional display screen and displayed, thereby efficiently performing an operation for determining whether an echo is a defect echo or a shape echo on the basis of the three-dimensional shape data. Thus, it is possible to quickly and easily specify the position of the defect in the object to be inspected.

Next, the configuration and operations of an ultrasonic inspection device according to a second embodiment of the present invention are described with reference to FIG. 10. The entire configuration of the ultrasonic inspection device according to the second embodiment is the same as that shown in FIG. 1.

Figure 10:
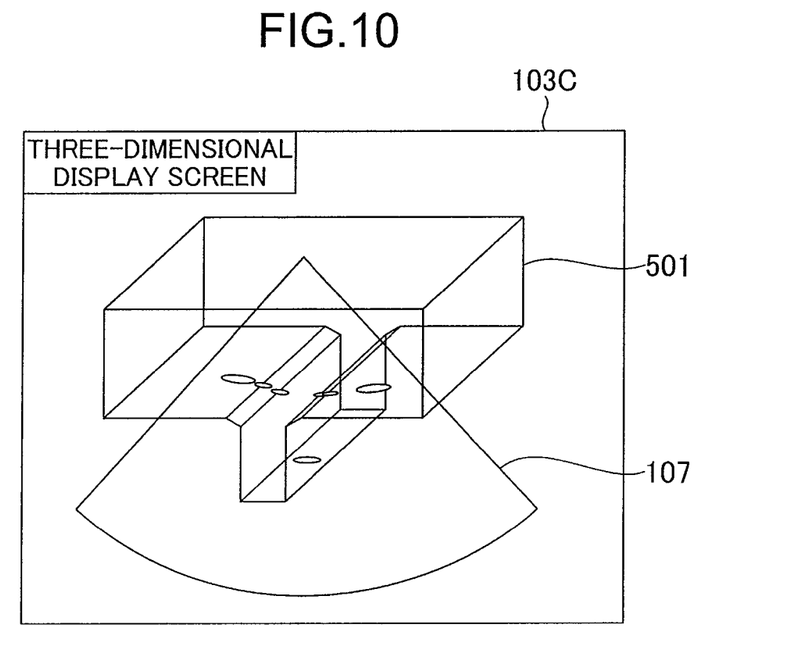
FIG. 10 is a diagram showing an example of display of two-dimensional inspection data and three-dimensional shape data in an ultrasonic inspection device according to a second embodiment of the present invention.

FIG. 10 is a diagram showing an example of display of two-dimensional inspection data and three-dimensional shape data in the ultrasonic inspection device according to the second embodiment.

The first embodiment describes the example of the position adjustment of the three-dimensional inspection data 401 and the three-dimensional shape data 501. On the other hand, the second embodiment describes an example of position adjustment of the two-dimensional inspection data and the three-dimensional shape data 501 that are acquired by a linear scanning method or a sector scanning method.

As a configuration of the ultrasonic inspection device and an automatic positioning method according to the second embodiment are the same as those according to the first embodiment, a description thereof is omitted. However, since the two-dimensional inspection data is output as image data of a pixel format or the like, a method for displaying results obtained after the position adjustment is different from that according to the first embodiment.

FIG. 10 shows the state in which the three-dimensional shape data 501 and a planar image of a sector 107 that is displayed as the two-dimensional inspection data are three-dimensionally displayed on the three-dimensional display screen 103C. The images of the sector 107 and of the three-dimensional shape data 501 can be displayed on the three-dimensional display screen 103C with an arbitrary enlargement or reduction rate by means of data input using the mouse 102F or the keyboard 102G which are connected to the calculator 102A. In addition, the colors and transparencies of the images of the sector 107 and the three-dimensional shape data 501 can be arbitrarily changed by means of data input using the mouse 102F or the keyboard 102G. The colors displayed can be changed according to reflection intensities. In this case, multiple color patterns are prepared so that the inspector can select a color pattern from the multiple color patterns on the basis of the purpose of use.

When the sector 107 and the three-dimensional shape data 501 are displayed in the aforementioned manner, the inspector can easily confirm a cross section of the object to be inspected to which the sector 107 corresponds. Though FIG. 10 shows the example in which only one sector is displayed, images of multiple sectors may be simultaneously displayed on the screen. An algorithm for three-dimensionally displaying the planar image is achieved by the aforementioned graphics APIs. Therefore, by using the graphics APIs in a program, providing necessary information such as dimensions of the planar image to be displayed, a viewpoint and a position of a planar image on the display screen and the like is provided, the planar image can be easily and three-dimensionally displayed on the three-dimensional display screen 103C together with the three-dimensional shape data 501 at an arbitrary position.

Next, a configuration and operations of an ultrasonic inspection device according to a third embodiment of the present invention are described with reference to FIG. 11. The entire configuration of the ultrasonic inspection device according to the third embodiment is the same as that shown in FIG. 1.

Figure 11:
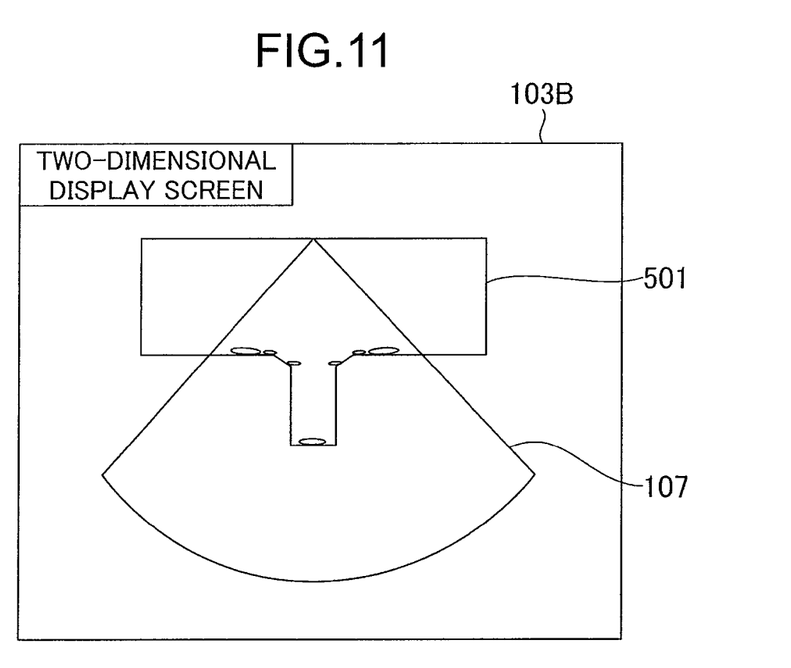
FIG. 11 is a diagram showing an example of display of two-dimensional inspection data and three-dimensional shape data in an ultrasonic inspection device according to a third embodiment of the present invention.

FIG. 11 is a diagram showing an example of display of two-dimensional inspection data and cross sectional position of three-dimensional shape data in the ultrasonic inspection device according to the third embodiment.

FIG. 11 shows the state in which a planar image of the sector 107 displayed as the two-dimensional inspection data and the three-dimensional shape data 501 are two-dimensionally displayed on the two-dimensional display screen 103B. The three-dimensional shape data 501 is displayed on the screen only an outline thereof in form of cross sectional view of a section to which the two-dimensional inspection data corresponds. Thus, the relationship between the cross section and the shape corresponding to the cross section can be easily recognized. The displaying of the outline of the cross sectional image of the three-dimensional shape data can be easily achieved by calculating lines of intersections of triangles constituting the STL data (three-dimensional shape data) and the cross-sectional planar image (two-dimensional inspection data) and drafting the calculated lines on the cross sectional image, for example. The drafting process uses the aforementioned graphics APIs.

As described above, according to the present embodiment, the two-dimensional inspection data that is generated from the waveforms of the multiple ultrasonic waves received by the ultrasonic probe is compared with the ultrasonic propagation analysis data pieces calculated by the ray tracing method on the basis of the three-dimensional shape data on the object to be inspected, and the three-dimensional shape data or the two-dimensional inspection data is automatically moved relative to the other data, thereby displaying the two-dimensional inspection data the two-dimensional inspection data overlapped with the outline of the cross sectional image of the three-dimensional shape data.

Next, a configuration and operations of an ultrasonic inspection device according to a fourth embodiment of the present invention are described with reference to FIGS. 12 and 13. The entire configuration of the ultrasonic inspection device according to the fourth embodiment is the same as that shown in FIG. 1.

Figure 12:
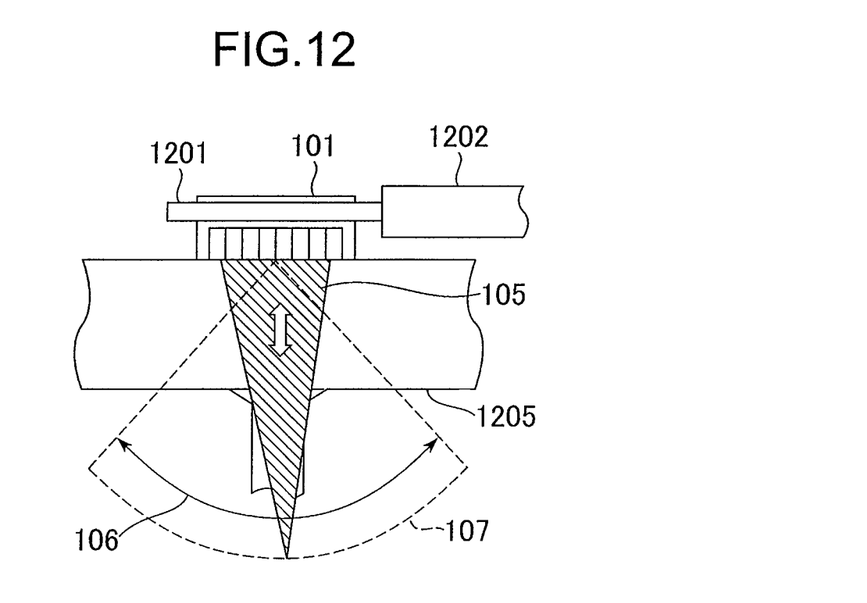
FIG. 12 is a diagram showing an array type ultrasonic probe and a moving unit that moves the array type ultrasonic probe, which are included in an ultrasonic inspection device according to a fourth embodiment of the present invention.
Figure 13:
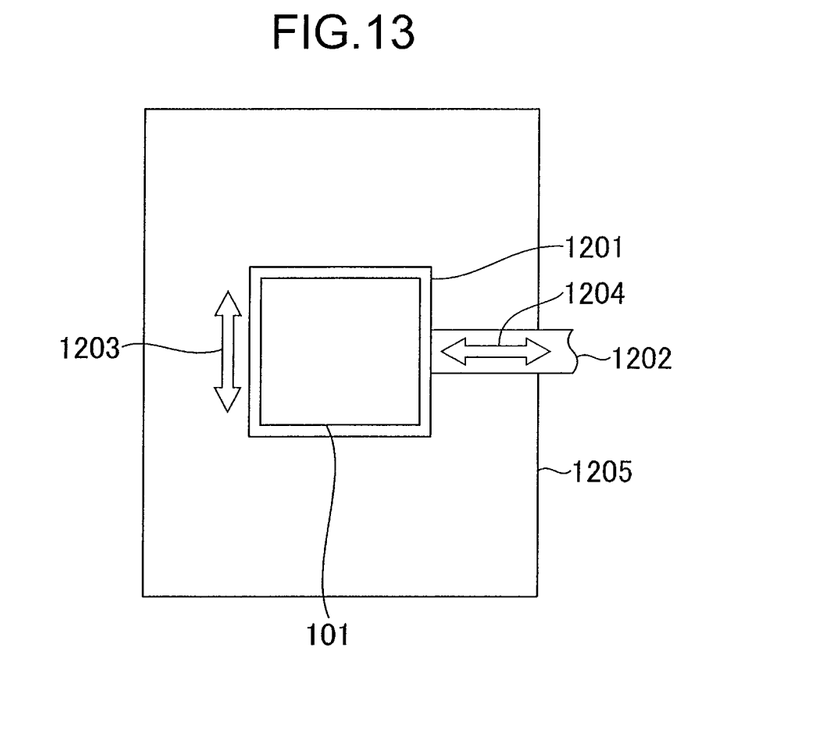
FIG. 13 is a diagram showing the array type ultrasonic probe and the moving unit that moves the array type ultrasonic probe, which are included in the ultrasonic inspection device according to the fourth embodiment.

FIGS. 12 and 13 are diagrams showing an array type ultrasonic probe and a moving unit that moves the ultrasonic type ultrasonic probe, which are included in the ultrasonic inspection device according to the fourth embodiment. FIG. 12 is a side view of the array type ultrasonic probe and the moving unit, while FIG. 13 is a top view thereof.

In the fourth embodiment, the array type ultrasonic probe 101 is fixed to the moving unit 1202 by means of a fixing jig 1201. The array type ultrasonic probe 101 is mechanically moved by control performed by an external device and receives signals of reflected ultrasonic waves. For example, the array type ultrasonic probe 101 is used for inspection of a welded line between a shroud support and a pressure container included in a BWR. The array type ultrasonic probe 101 can be moved freely on a pressure container 1205 in a direction 1203 extending along the welded line between the shroud support and the pressure container and in a direction 1204 perpendicular to the welded line, by the moving unit 1202. The array type ultrasonic probe 101 transmits and receives ultrasonic signals while moving.

The basic configuration of the ultrasonic inspection device and an automatic position adjustment method according to the present embodiment are the same as those according to the first embodiment. For example, when the array type ultrasonic probe 101 moves while performing sector scanning and collecting data, an image of the sector 107 is displayed, on an as-needed basis, as the two-dimensional inspection data on the two-dimensional display screen 103B together with the outline of the cross sectional image of the three-dimensional shape data 501, through the automatic position adjustment process according to the present invention.

In addition, the array type ultrasonic probe 101 performs sector scanning while moving so that the probe 101 acquires a predetermined number of images of sectors. After that, the calculator 102A generates three-dimensional inspection data 401, performs the automatic position adjustment process according to the present invention, and then, causes the three-dimensional inspection data 401 to be displayed on an as-needed basis together with the three-dimensional shape data 501 on the three-dimensional display screen 103C. According to the present embodiment, the display results can be confirmed while echoes and the shape of the object to be inspected are simultaneously displayed, thereby significantly improving the efficiency of the inspection.

As described above, according to the present embodiment, the ultrasonic inspection device includes the moving unit that is fixed to the ultrasonic probe and moves the ultrasonic probe in any direction. Further, the ultrasonic inspection device according to the present embodiment can display the inspection data overlapped with the three-dimensional shape data.

What is claimed is:

1. An ultrasonic inspection method comprising the steps of:
preparing an ultrasonic probe having a plurality of piezoelectric elements;
scanning an inspection object with the ultrasonic probe having the plurality of piezoelectric elements according to a scanning method;
receiving ultrasonic waves from the inspection object with the ultrasonic probe having the plurality of piezoelectric elements;
generating three-dimensional ultrasonic inspection data from waveforms of the ultrasonic waves received by the ultrasonic probe;
calculating a plurality of ultrasonic propagation data on the basis of three-dimensional shape data of the inspection object and the scanning method by sequentially changing ultrasonic wave incident points and ultrasonic wave incident directions;
comparing the three-dimensional ultrasonic inspection data with the plurality of ultrasonic propagation data to match a combination of the three-dimensional ultrasonic inspection data with a portion of the plurality of ultrasonic propagation data; and
displaying the three-dimensional ultrasonic inspection data and the three-dimensional shape data in such a manner as to move on a display screen a position at which to display the three-dimensional ultrasonic inspection data or the three-dimensional shape data on the basis of the combination of the three-dimensional ultrasonic inspection data and the portion of the ultrasonic propagation data which match each other.

2. The ultrasonic inspection method according to claim 1, further comprising the steps of:
calculating differences between the three-dimensional ultrasonic inspection data and the plurality of ultrasonic propagation data;
specifying the portion of the ultrasonic propagation data from which the smallest difference among the calculated differences has been calculated.

3. The ultrasonic inspection method according to claim 2, further comprising the steps of:
calculating a mutual correlation function from the three-dimensional ultrasonic inspection data and the ultrasonic propagation data;
calculating a power spectral density function from the mutual correlation function;
calculating differences between the three-dimensional ultrasonic inspection data and the ultrasonic propagation data on the basis of the power spectral density function; and
specifying the portion of the ultrasonic propagation data from which the smallest difference among the calculated differences has been calculated.

4. The ultrasonic inspection method according to claim 3, further comprising the steps of:
moving in parallel and rotating the three-dimensional ultrasonic inspection data or the three-dimensional shape data relative to the other data so that an ultrasonic wave incident point and an ultrasonic wave incident direction of the specified portion of the ultrasonic propagation data match an ultrasonic wave incident point and ultrasonic wave incident direction of the three-dimensional shape data; and displaying the three-dimensional ultrasonic inspection data and the three-dimensional shape data while the three-dimensional ultrasonic inspection data and the three-dimensional shape data overlap each other.

5. An ultrasonic inspection method comprising the steps of:
preparing an ultrasonic probe having a plurality of piezoelectric elements;
scanning an inspection object with the ultrasonic probe having the plurality of piezoelectric elements according to a scanning method;
receiving ultrasonic waves from the inspection object with the ultrasonic probe having the plurality of piezoelectric elements;
generating two-dimensional ultrasonic inspection data from waveforms of the ultrasonic waves received by the ultrasonic probe;
calculating a plurality of ultrasonic propagation data on the basis of three-dimensional shape data of the inspection object and the scanning method by sequentially changing ultrasonic wave incident points and ultrasonic wave incident directions;
comparing the two-dimensional ultrasonic inspection data with the plurality of ultrasonic propagation data to match a combination of the two-dimensional ultrasonic inspection data with a portion of the plurality of ultrasonic propagation data;
moving a position at which to display the two-dimensional ultrasonic inspection data or the three-dimensional shape data relative to a position of the other of the two-dimensional ultrasonic inspection data or the three-dimensional shape data on a display screen on the basis of the combination of the two-dimensional ultrasonic inspection data and the portion of the plurality of the ultrasonic propagation data which match each other; and
three-dimensionally displaying the two-dimensional ultrasonic inspection data and the three-dimensional shape data while the two-dimensional ultrasonic inspection data and the three-dimensional shape data overlap each other.

6. An ultrasonic inspection method comprising the steps of:
preparing an ultrasonic probe having a plurality of piezoelectric elements;
scanning an inspection object with the ultrasonic probe having the plurality of piezoelectric elements according to a scanning method;
receiving ultrasonic waves from the inspection object with the ultrasonic probe having the plurality of piezoelectric elements
generating two-dimensional ultrasonic inspection data from waveforms of the ultrasonic waves received by the ultrasonic probe;
calculating a plurality of ultrasonic propagation data on the basis of three-dimensional shape data of the inspection object and the scanning method by sequentially changing ultrasonic wave incident points and ultrasonic wave incident directions;
comparing the two-dimensional ultrasonic inspection data with the plurality of ultrasonic propagation data to match a combination of the two-dimensional ultrasonic inspection data with a portion of the plurality of ultrasonic propagation data;
moving a position at which to display the two-dimensional ultrasonic inspection data or the three-dimensional shape data relative to a position of the other of the two-dimensional ultrasonic inspection data or the three-dimensional shape data on a display screen on the basis of the combination of the two-dimensional ultrasonic inspection data and the portion of the plurality of the ultrasonic propagation data which match each other; and
displaying the two-dimensional inspection data and an outline of a cross sectional image of the three-dimensional shape data in an overlapping manner.

7. The ultrasonic inspection method according to claim 1, wherein the ultrasonic propagation data are calculated by a ray tracing method on the basis of the three-dimensional shape data of the inspection object.

8. An ultrasonic inspection device comprising:
an ultrasonic probe that includes a plurality of piezoelectric elements;
a pulser that supplies transmission signals to the respective piezoelectric elements of the ultrasonic prove according to a scanning method to scan the inspection object;
a receiver that receives signals from the respective piezoelectric elements of the ultrasonic prove;
a delay time controller that sets delay times which are different from each other for each of the piezoelectric elements, to the transmission signals and to the signals received by the piezoelectric elements;
a data storage unit that stores the waveforms of ultrasonic waves received by the ultrasonic probe;
a calculator that is provided for image processing and includes a processor and memory which generates inspection data of an inspection object from the waveforms stored in the data storage unit, and calculates ultrasonic propagation data on the basis of three-dimensional shape data of the inspection object and the scanning method by sequentially changing ultrasonic wave incident points and ultrasonic wave incident directions;
a display unit that simultaneously displays the three-dimensional shape data of the inspection object and the inspection data; and
wherein the calculator further compares the inspection data with the plurality of ultrasonic propagation data to match a combination of the inspection data with a portion of the plurality of ultrasonic propagation data, and
wherein the display unit has a position correcting function of automatically moving positions of the three-dimensional shape data and the inspection data relative to each other on a display screen on the basis of the combination of the inspection data and the portion of the plurality of the ultrasonic propagation data which match each other.

9. The ultrasonic inspection device according to claim 8, further comprising a moving unit that is fixed to the ultrasonic probe and moves the ultrasonic probe in any direction,
wherein the inspection data and the three-dimensional shape data are displayed while overlapping each other.

10. The ultrasonic inspection device according to claim 8, further comprising a moving unit that is fixed to the ultrasonic probe and moves the ultrasonic probe in any direction,
wherein the inspection data and an outline of a cross sectional image of the three-dimensional shape data are displayed while overlapping each other.

11. The ultrasonic inspection device according to claim 8, wherein the ultrasonic propagation data are calculated by a ray tracing method on the basis of the three-dimensional shape data.

* * * * *